United States Patent [19]

Mussinan et al.

[11] 4,139,541
[45] Feb. 13, 1979

[54] MALTOL-2-METHYL PENTENOATES AND ORGANOLEPTIC USES THEREOF

[75] Inventors: Cynthia J. Mussinan, Bricktown; Braja D. Mookherjee, Holmdel, both of N.J.; Alfred E. Goossens, New York, N.Y.; Manfred H. Vock, Locust, N.J.

[73] Assignee: International Flavors & Fragrances Inc., New York, N.Y.

[21] Appl. No.: 884,382

[22] Filed: Mar. 8, 1978

[51] Int. Cl.² ............................................. C07D 309/22
[52] U.S. Cl. .............................. 260/345.8 R; 426/536
[58] Field of Search ................................. 260/345.8 R

[56] References Cited
U.S. PATENT DOCUMENTS 3,907,718  9/1975  Hall et al. ........................... 560/205

*Primary Examiner*—Nicky Chan
*Attorney, Agent, or Firm*—Arthur L. Liberman; Franklin D. Wolffe; Harold Haidt

[57] ABSTRACT

Described are maltol-2-methyl pentenoates having the structure:

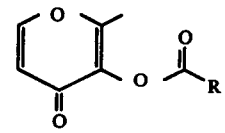

wherein R is a secondary pentenyl moiety having one of the structures:

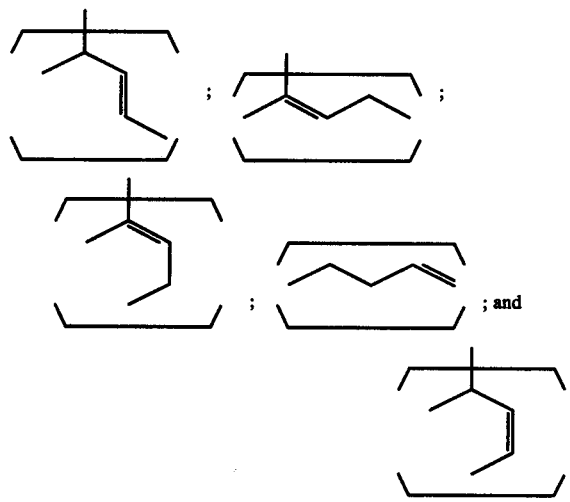

as well as methods for preparing foodstuffs, flavoring compositions for foodstuffs, chewing gum compositions, flavoring compositions for chewing gum, medicinal product compositions and ingredients for medicinal product compositions by including therein said maltol-2-methyl pentenoates which augment or enhance the flavor or aroma of said compositions.

5 Claims, 8 Drawing Figures

GLC PROFILE FOR EXAMPLE I

IR SPECTRUM FOR EXAMPLE I

GLC PROFILE FOR EXAMPLE II

FIG. 6 IR SPECTRUM FOR EXAMPLE II

GLC PROFILE FOR EXAMPLE III

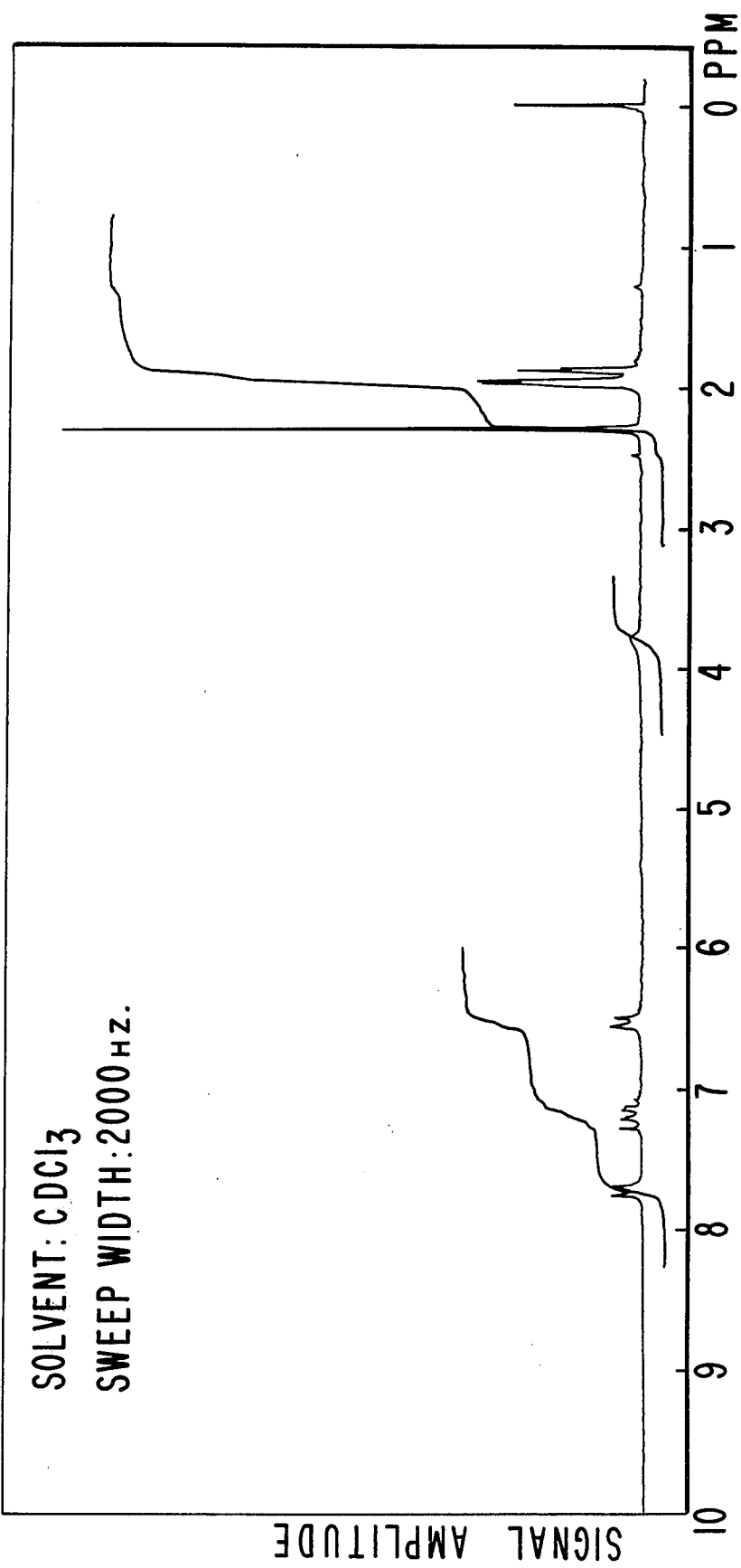

MALTOL-2-METHYL PENTENOATES AND ORGANOLEPTIC USES THEREOF

BACKGROUND OF THE INVENTION

The present invention relates to maltol-2-methyl pentenoates and novel compositions using such maltol-2-methyl pentenoates to augment or enhance the flavor or aroma of foodstuffs, chewing gums and medicinal products.

There has been considerable work performed relating to substances which can be used to impart (or enhance) flavors to (or in) various consumable materials, e.g., foodstuffs, medicinal products and chewing gums. These substances are used to diminish the use of natural materials, some of which may be in short supply and to provide more uniform properties in the finished product. Sweet, strawberry-like, fruity, red berry, green, winey and cognac-like aromas as well as sweet, fruity, strawberry, berry and winey tastes are particularly desirable for many uses in foodstuff flavors, medicinal product flavors and chewing gum flavors; particularly strawberry flavors, raspberry flavors, wine flavors and cognac flavors.

U.S. Pat. No. 4,000,327 issued on Dec. 28, 1976 describes the use in berry fruit flavors of a synthetically produced 6-carbon carboxylic acid ester-containing composition comprising as its major constituent a cis-ester of 2-methyl-3-pentenoic acid having the structure:

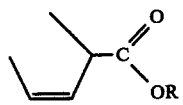

wherein R is one of ethyl, isobutyl or n-hexyl.

U.S. Pat. No. 3,499,769 issued on Mar. 10, 1970 discloses processes for imparting a fresh fruity flavor (particularly strawberry flavor) to foods by adding a small amount of 2-methyl-2-pentenoic acid to the foodstuff. In U.S. Pat. No. 3,499,769 it is emphasized that the basic nuance imparted by 2-methyl-2-pentenoic acid is a "berry" flavor.

Maltol, having the structure:

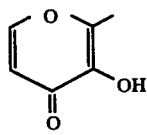

is well known for its use in strawberry flavors. It is described by Arctander, "Perfume and Flavor Chemicals (Aroma Chemicals)" at number 1831 to have a warm fruity, caramellic-sweet odor with emphasis on the caramellic note in the dry state. Solutions of maltol are indicated by Arctander to show a pronounced fruity, jam-like odor of pineapple, strawberry types. Arctander further states that maltol is "intensely sweet, fruity, jam-like, . . . having a pineapple, strawberry type flavor with caramellic undertone". It is stated that the caramellic effect is predominant at high (20–100 ppm) concentrations while the fruity effect is most attractive at much lower concentrations. It is stated by Arctander that the main use of maltol is in flavor compositions not only as a fruity component in pineapple and strawberry, but in general, as a sweetener.

In addition, maltyl esters of alkanoic acids are known as flavorants. Thus, on the GRAS list (generally recognized as safe by the Flavor Extracts Manufacturers' Association) maltyl isobutyrate (number 3462, Food Technology, August 1975, page 72) is set forth. On that same page, 2-methyl-3-pentenoic acid is set forth as number 3464.

U.S. Pat. No. 2,766,148 issued on Oct. 9, 1956 sets forth the improvement in the flavor and aroma of tobacco by addition thereto of from 0.01 up to 1.0% of esters including maltol-3-methyl-valerate.

None of the prior art however sets forth compounds having structures related to the maltol-2-methyl pentenoates of the present invention. Furthermore, the properties of the maltol-2-methyl pentenoates of the present invention, from an organoleptic standpoint, are considered to be unobvious, unexpected and advantageous with respect to the organoleptic properties of the esters of the prior art set forth above.

BRIEF DESCRIPTION OF THE DRAWINGS

FIG. 8 represents the NMR spectrum for the reaction product of Example III, which is maltyl tiglate.

THE INVENTION

Figure 1:
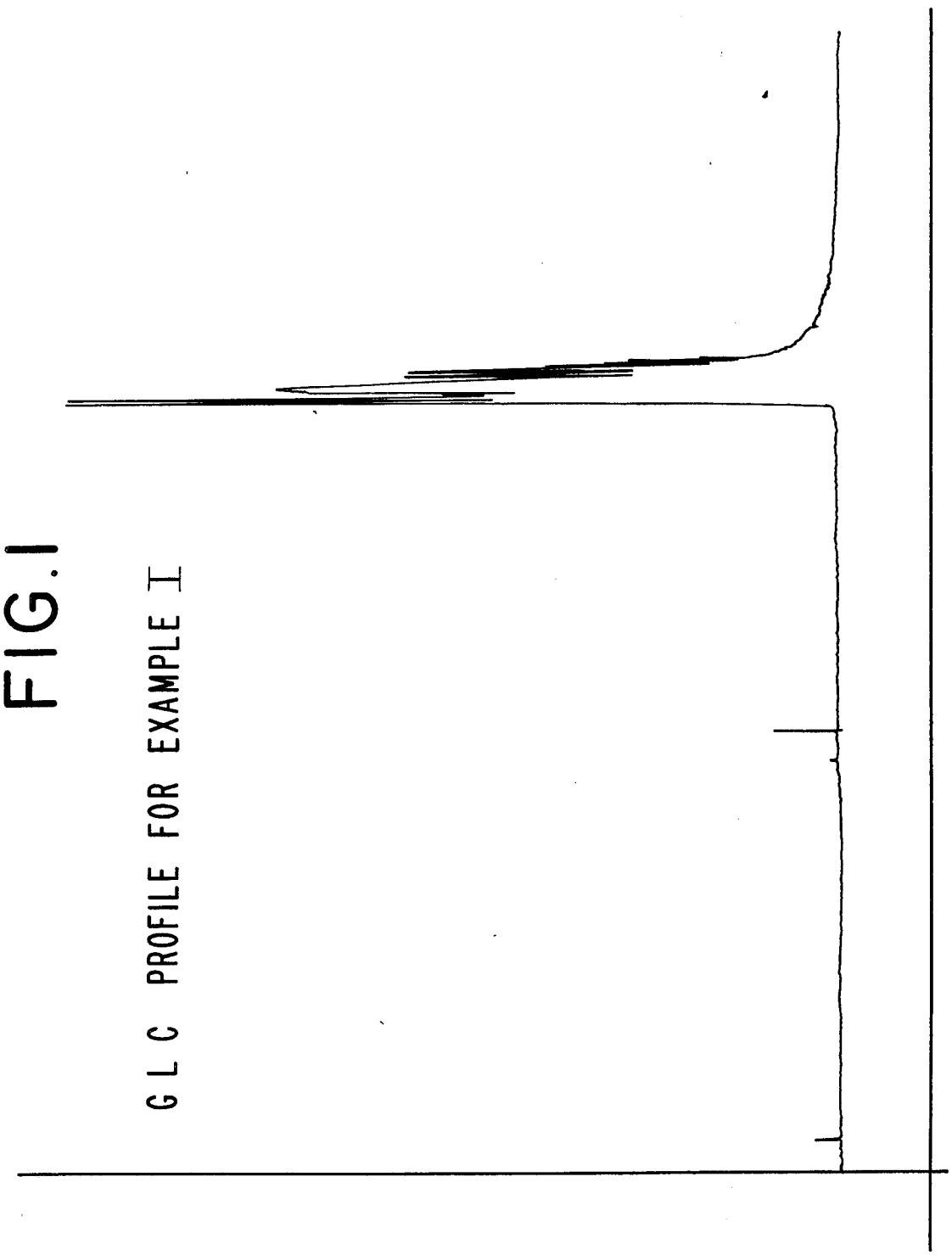
FIG. 1 represents the GLC profile for the reaction product of Example I, which is maltyl-2-methyl-3-pentenoate having a high proportion (greater than 50%) of maltyl-2-methyl-cis-3-pentenoate.

This invention relates to maltol-2-methyl pentenoates having the generic structure:

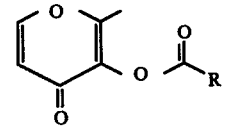

wherein R represents a secondary pentyl moiety having one of the structures:

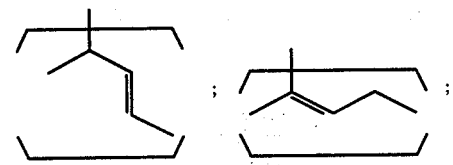

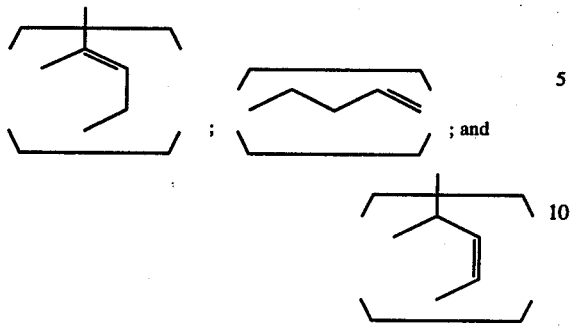

It has now been discovered that solid and liquid foodstuffs, chewing gums, medicinal products and flavoring compositions therefor having sweet, strawberry-like, fruity, red berry, green, winey and cognac-like aromas and sweet, fruity, strawberry, berry and winey tastes may be provided by the utilization of maltol-2-methyl pentenoates.

The maltol-2-methyl pentenoates of our invention may be prepared by reacting maltol with the appropriate acyl halide which, in turn, may be formed from the corresponding alkenoic acid with thionyl chloride ($SOCl_2$). This reaction sequence is generically set forth as follows:

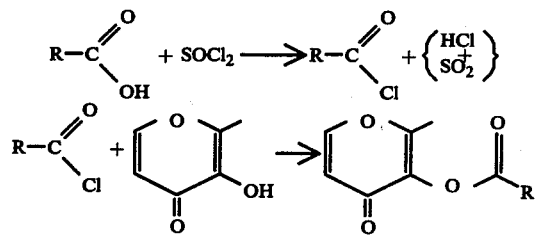

wherein R is one of the moieties:

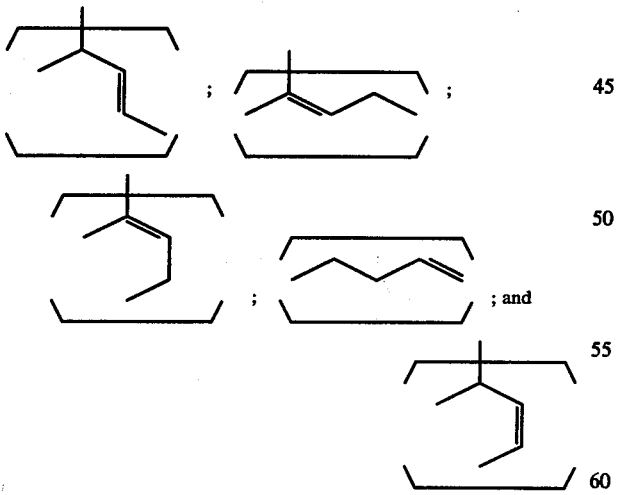

In place of thionyl chloride, thionyl bromide may be used and the corresponding acyl bromide may be reacted with maltol.

Although the maltol-2-methyl pentenoates of our invention are novel, the processes for preparing same as set forth above and conditions for such processes are set forth in "Reagents for Organic Synthesis", Fieser & Fieser, John Wiley & Sons, Inc. publishing company, 1967 at pages 1158 and 1159 and "Organic Syntheses Collective Volume III", E. C. Horning, John Wiley & Sons, Inc. publishing company, 1955 at pages 714 and 715.

Examples of the maltol-2-methyl pentenoates of our invention and their organoleptic properties are as follows:

| Name and Structure | Organoleptic Properties |
| --- | --- |
| Maltol-2-methyl-2-pentenoate (a mixture of compounds having the structures: ![structure] cis and trans isomers) | A fruity, berry, yeasty, winey, strawberry, maltol-like and cognac aroma with a fruity, berry, yeasty, winey, strawberry-like and allium taste at 10 ppm. |
| Maltol-2-methyl-3-pentenoate (a mixture of compounds having the structures: ![structure] cis and trans isomers) | A sweet, fruity, strawberry-like and red berry aroma characteristic with sweet, fruity and strawberry flavor characteristics and green nuances at 5 ppm. |

Accordingly, the maltol-2-methyl pentenoates of our invention contemplate mixtures of cis and trans isomers and the individual cis and trans isomers themselves. Thus, the specific cis and transisomer structures of our invention are as follows:

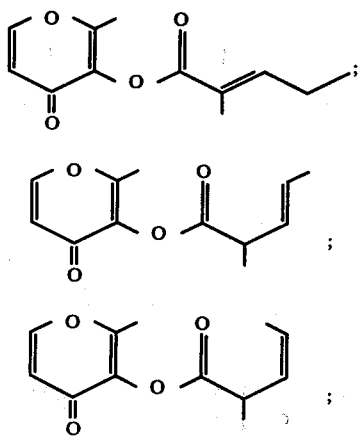

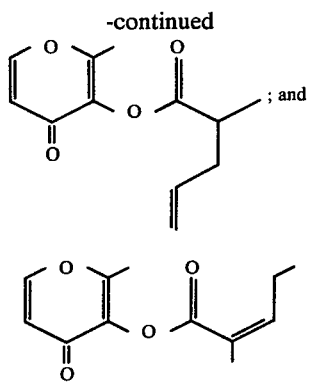
; and

When the maltol-2-methyl pentenoates of our invention are used as a food flavor adjuvant, or a chewing gum flavor adjuvant or a medicinal product flavor adjuvant, the nature of the co-ingredients included with the said maltol-2-methyl pentenoates in formulating the product composition will also serve to alter the organoleptic characteristics of the ultimate foodstuff or chewing gum or medicinal product treated therewith.

As used herein, in regard to flavors the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste."

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible materials which have medicinal value such as cough syrups, cough drops, laxatives, aspirin, chewable medicinal tablets containing antibiotics and sore throat lozenges.

The term "chewing gum" is herein intended to be definitive of a composition which comprises a substantially water-insoluble, chewable, plastic gum base such as chicle, or substitutes therefor, including jelutong, guttakay rubber or certain comestible natural or synthetic resins or waxes. Incorporated with the gum base, and in admixture therewith, may be plasticizers or softening agents, e.g., glycerine; and a flavoring composition which incorporates the maltol-2-methyl pentenoates of our invention, and in addition sweetening agents which may be sugars including sucrose or dextrose and/or artificial sweeteners such as cyclamates or saccharin. Other optional ingredients may also be present.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g, sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl acrolein, n-hexanal, 2-hexenal, cis-3-hexenal, 2-heptanal, 4-(p-hydroxyphenyl)-2-butanone, alpha-ionone, beta-ionone, 2-methyl-3-butanone, 2-pentanone, 2-pentenal and propanal; alcohols, such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, medicinal product or chewing gum, whether simulated or natural, and should, in any event, be capable of providing an environment in which the maltol-2-methyl pentenoates of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff or chewing gum or medicinal product to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of maltol-2-methyl pentenoates employed in a particular instance can vary over a relatively wide range whereby to its desired organoleptic effects having reference to the nature of the product are achieved. All parts and percentages given herein are by weight unless otherwise specified. Thus, correspondingly greater amounts would be necessary in those instances wherein the ultimate food composition or chewing gum composition or medicinal product composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se, chewing gum per se, medicinal product per se or flavoring composition. Thus, the use of insufficient quantities of maltol-2-methyl pentenoates of our invention will, of course, substantially vitiate any possibility of obtaining the desired results while excess quantities prove needlessly costly and in extreme cases, may disrupt the flavor-aroma balance, thus proving self-defeating. Accordingly, the terminology, "effective amount" and "sufficient amount" is to be accorded a significance in the context of the present invention consistent with the obtention of desired flavoring effects.

Thus, and with respect to ultimate food compositions, ultimate chewing gum compositions and ultimate medicinal product compositions, it is found that quantities of maltol-2-methyl pentenoates ranging from a small but effective amount, e.g., 0.01 parts per million up to about 50 parts per million by weight based on total composition are suitable. Concentrations in excess of the maximum quantity stated are not normally recommended since they fail to prove commensurate enhancement of organoleptic properties. In those instances wherein the maltol-2-methyl pentenoates are added to the foodstuff or chewing gum or medicinal product, as the case may be, as an integral component of a flavoring composition, it is, of course, essential that the total quantity of flavoring composition employed be sufficient to yield an effective maltol-2-methyl pentenoate concentration in the foodstuff product, medicinal product or chewing gum.

Medicinal product, chewing gum and food flavoring compositions prepared in accordance with the present invention preferably contain the maltol-2-methyl pentenoates in concentrations ranging from about 0.15% up to about 10% by weight based on the total weight of said flavoring composition.

The compositions described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, the flavoring compositions in the form of particulate solids can be conveniently prepared by mixing the maltol-2-methyl pentenoates with, for example, gum arabic, gum tragacanth, carrageenan and the like, and thereafter spray-drying the resultant mixture whereby to obtain the particular solid product. Pre-prepared flavor mixes in powder form, e.g., a vanilla powder mix or a walnut flavored powder mix are obtained by mixing the dried solid components, e.g., starch, sugar and the like and maltol-2-methyl pentenoates of our invention in a dry blender until the requisite degree of uniformity is achieved.

It is presently preferred to combine with the maltol-2-methyl pentenoates of our invention the following adjuvants:

Geraniol
Ethyl methyl phenyl glycidate
Vanillin
Ethyl pelargonate
Isoamyl acetate
Ethyl butyrate
Maltol
Naphthyl ethyl ether
Ethyl acetate
Isoamyl butyrate
2-Methyl-2-pentenoic acid
Elemecine (4-allyl-1,2,6-trimethoxy benzene)
Isoelemecine (4-propenyl-1,2,6-trimethoxy benzene)
High cis 2-methyl-3-pentenoic acid isomer mixtures produced according to U.S. Pat. No. 3,984,579
Ethyl-2-methyl-cis-3-pentenoic acid ester produced according to U.S. Pat. No. 4,000,327
Isobutyl-2-methyl-cis-3-pentenoic acid ester produced according to U.S. Pat. No. 4,000,327
n-Hexyl-2-methyl-3-pentenoic acid ester produced according to U.S. Pat. No. 4,000,327
Maltol isobutyrate The following Examples are given to illustrate embodiments of the invention as it is presently preferred to practice it. The following Examples are given to illustrate methods for preparing maltol-2-methyl pentenoates useful in the practice of our invention. It will be understood that these Examples are illustrative, and the invention is not to be considered as restricted thereto except as indicated in the appended claims.

EXAMPLE I

PREPARATION OF MALTYL-2-METHYL-CIS-3-PENTENOATE MIXTURE

Reaction

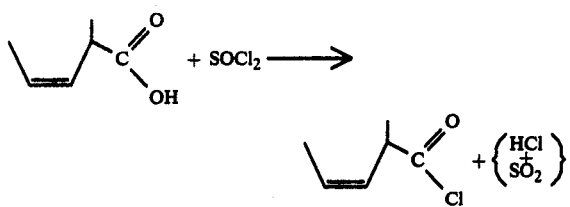

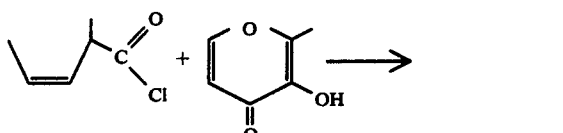

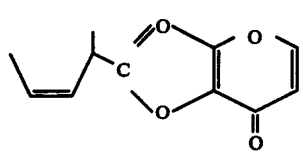

Procedure

Into a 250 ml two necked reaction flask equipped with mechanical stirrer, Fredrich's condenser and gas trap, 12 g of a mixture containing a high proportion of 2-methyl-cis-3-pentenoic acid prepared according to Example VII at column 18 of U.S. Pat. No. 3,984,579 issued on Oct. 5, 1976, in 50 ml benzene is added. Fredrich's condenser side arm is equipped in such a way as to vent the gases released through a trap into a beaker containing commercial preparation of sodium hypochlorite (Clorox ®). With vigorous stirring, 11.9 grams of freshly distilled thionyl chloride are added to the reaction mixture. The reaction mixture is then stirred and heated until no more hydrogen chloride or sulfur dioxide gas is released (over a period of 45 minutes). The reaction mass is then allowed to cool and 12.6 grams of maltol and 50 ml of benzene are added thereto. The mixture is again heated until no more gas evolves (period of time: 45 minutes). The benzene solvent is then removed on a rotary evaporator. The resulting reaction product, maltyl-2-methyl-3-pentenoate containing a high proportion (80%) of maltyl-2-methyl-cis-3-pentenoate and 20% maltyl-2-methyl-trans-3-pentenoate is trapped on a preparative GLC column. Conditions: 12' × ¼" 20% SE-52 column programmed at 100–190° C. at 8° C. per minute.

A total of 0.55 grams of maltyl-2-methyl-3-pentenoate is collected having a purity of greater than 99%.

Figure 2:
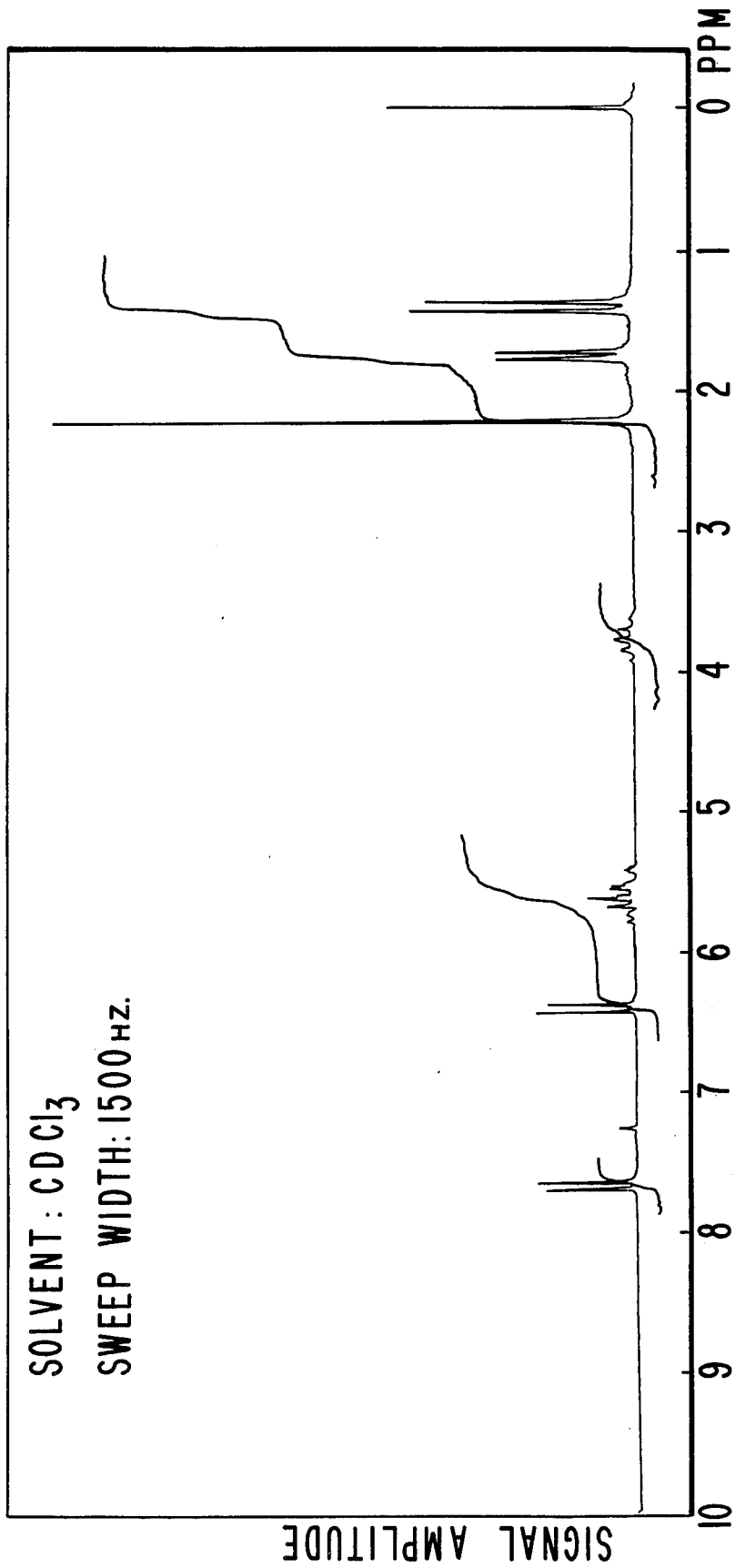
FIG. 2 represents the NMR spectrum for maltyl-2-methyl-3-pentenoate produced according to Example I.
Figure 3:
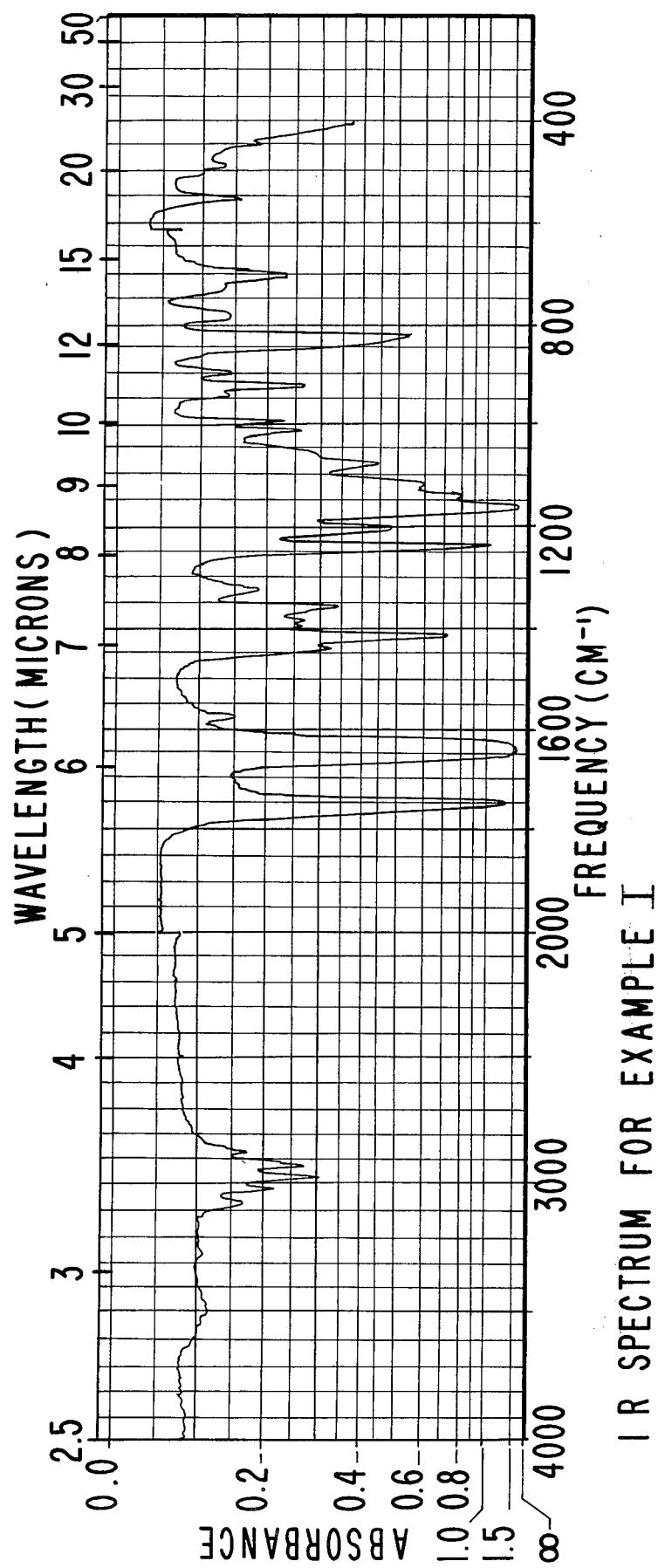
FIG. 3 represents the Infrared spectrum for the reaction product of Example I, which is maltyl-2-methyl-3-pentenoate.

The GLC profile for the reaction product is set forth in FIG. 1. The NMR spectrum is set forth in FIG. 2. The Infrared spectrum for maltyl-2-methyl-3-pentenoate is set forth in FIG. 3.

EXAMPLE II

PREPARATION OF MALTYL-2-METHYL-2-PENTENOATE

Reaction

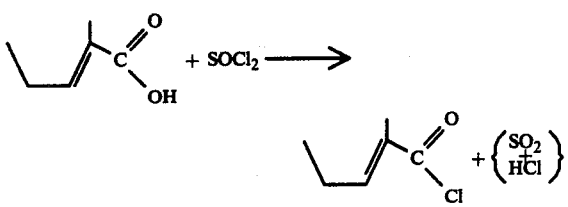

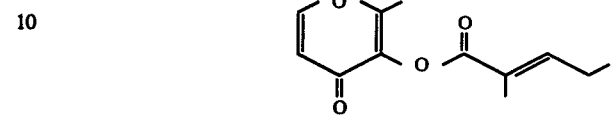

Procedure

119 Grams of thionyl chloride is distilled immediately before using (75–76° C. at 760 mm pressure). While the thionyl chloride is being distilled, 114 grams of 2-methyl-2-pentenoic acid (mixture of cis and trans isomers prepared according to the procedure of U.S. Pat. No. 3,499,769 issued on Mar. 10, 1970) is melted using warm water. The melted 2-methyl-2-pentenoic acid and distilled thionyl chloride are then slowly added to a 1 liter three necked round bottomed flask equipped with a mechanical stirrer and a Fredrich's condenser, the side arm of which is equipped with a trap to vent the gas released into a beaker of 5% sodium carbonate. The mixture is stirred and heated for a period of 1 hour. The mixture is then cooled and maltol (126 grams) dissolved in 200 cc of benzene is added. The reaction mass is then heated to reflux and stirred for a period of two hours. After cooling, the reaction mass is filtered to recover a maltol precipitate. The supernatant liquid is then added to a separatory funnel and extracted with three volumes of 5% sodium carbonate. The supernatant liquid is then washed with water. The benzene is then removed using a rotary evaporator and the resulting product is recrystallized from ethyl acetate. The sodium carbonate layer is acidified with 2 molar aqueous hydrochloric acid and extracted with 10% volumes of diethyl ether; then washed with water and dried over anhydrous sodium sulfate; then concentrated to 3.60 grams of residue. This residue is determined to be 2-methyl-2-pentenoic acid.

The recrystallization product from ethyl acetate weighs 30.62 grams and is identified as maltyl-2-methyl-2-pentenoate having a purity of 99.46% (yield: 13.8%).

Figure 4:
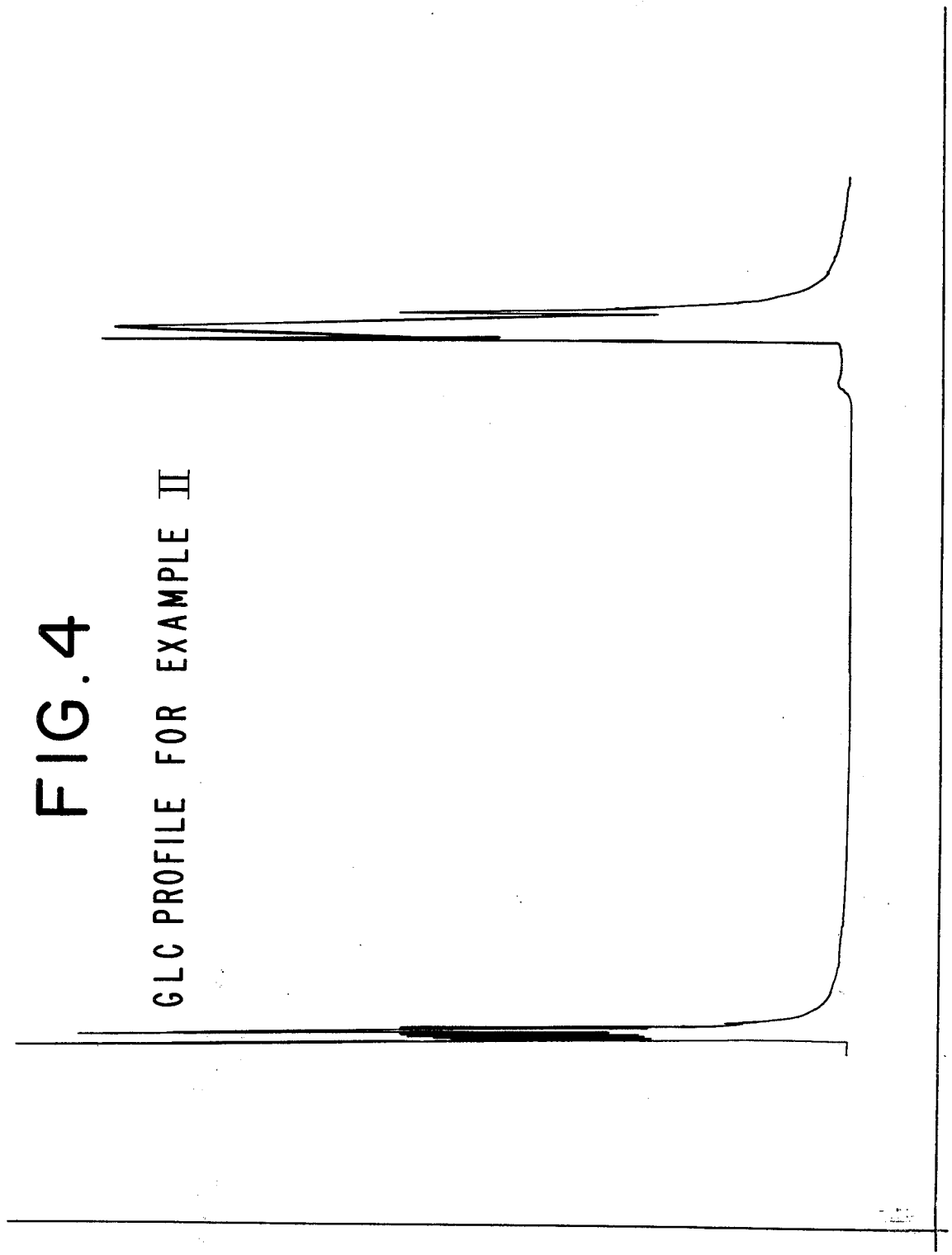
FIG. 4 represents the GLC profile for the reaction product of Example II, which is maltyl-2-methyl-2-pentenoate.
Figure 5:
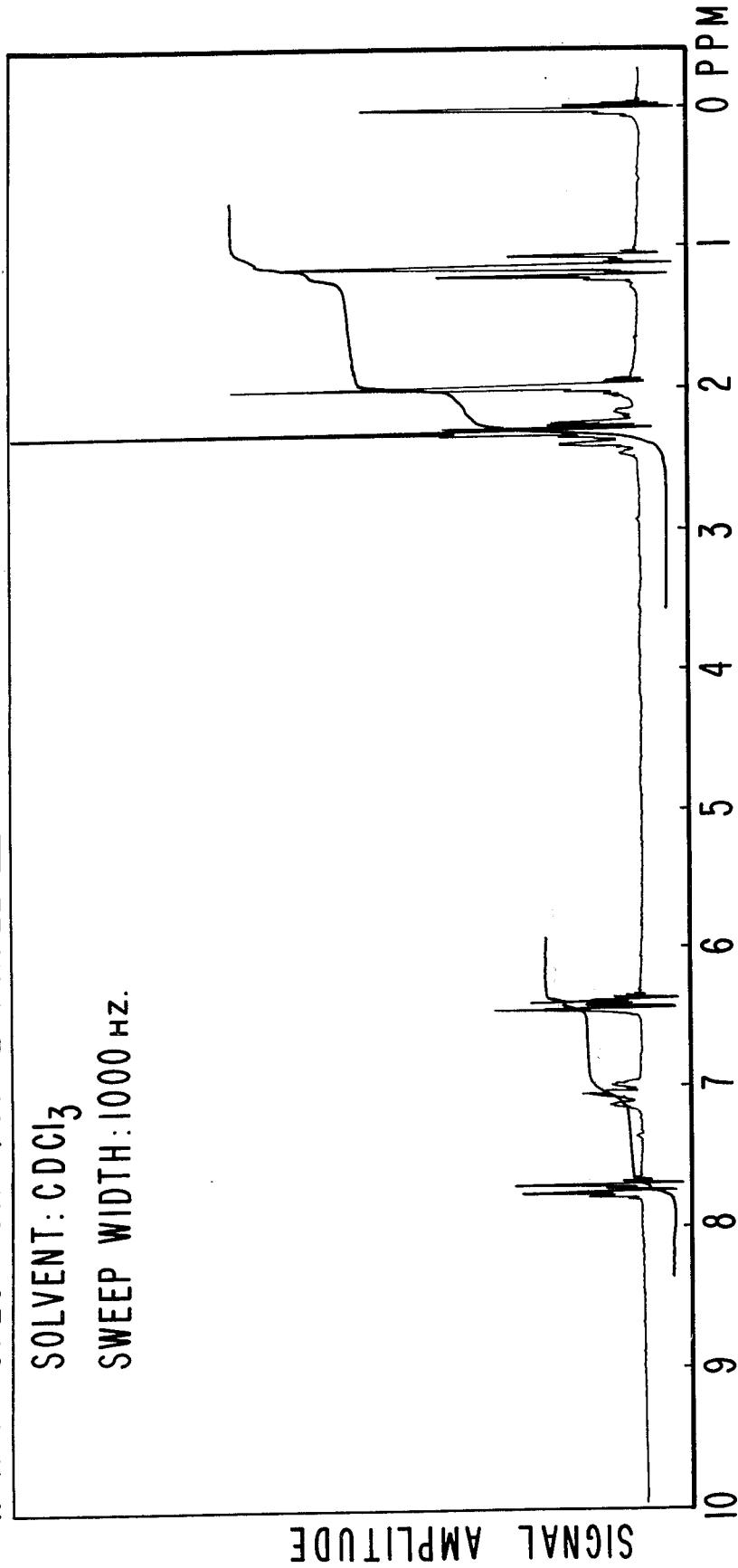
FIG. 5 represents the NMR spectrum for the reaction product of Example II, which is maltyl-2-methyl-2-pentenoate.
Figure 6:
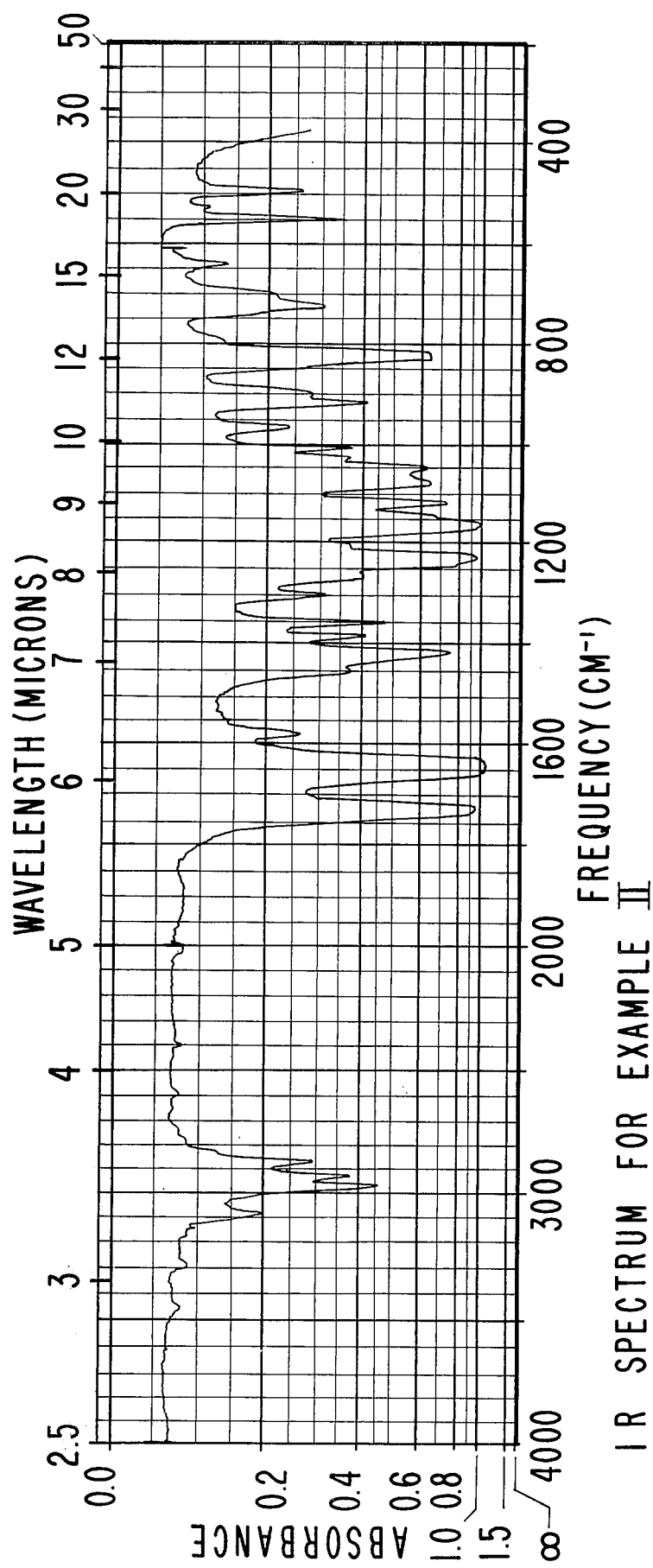
FIG. 6 represents the Infrared spectrum for the reaction product of Example II, which is maltyl-2-methyl-2-pentenoate.

The GLC profile for the reaction product containing maltyl-2-methyl-2-pentenoate is set forth in FIG. 4. The NMR spectrum for maltyl-2-methyl-2-pentenoate is set forth in FIG. 5. The Infrared spectrum for maltyl-2-methyl-2-pentenoate is set forth in FIG. 6.

EXAMPLE III

PREPARATION OF MALTYL TIGLATE

Reaction

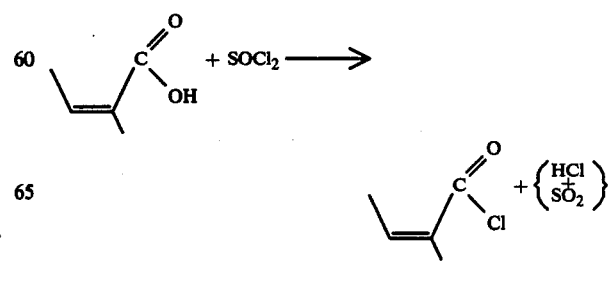

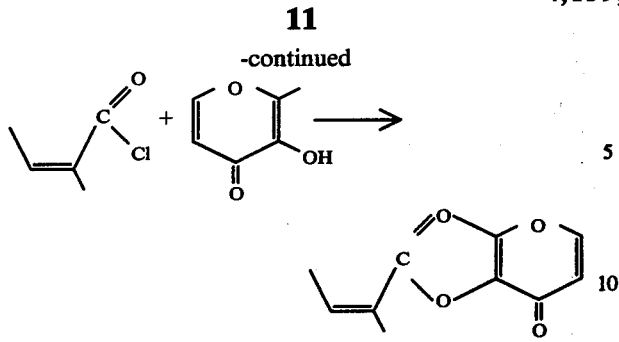

Procedure

10 Grams of tiglic acid dissolved in 50 ml anhydrous benzene are placed in a 250 ml two necked reaction flask equipped with mechanical stirrer and Fredrich's condenser, whose side arm is equipped in such a way as to vent the gases released during the reaction through a trap and into a beaker containing a solution of sodium hypochlorite (Clorox®). 11.9 Grams of thionyl chloride (freshly distilled) are added to the reaction mass. The mixture is then stirred and heated until no additional hydrogen chloride or sulfur dioxide is released (period: 60 minutes). The reaction mass is then allowed to cool and 12.6 grams of maltol and 50 cc of benzene are added. The reaction mass is then heated to reflux until no more sulfur dioxide or hydrogen chloride gas is released (period: 1 hour). The benzene is removed on a rotary evaporator.

The reaction mass solidifies upon refrigeration and is then dissolved in ethyl acetate and placed in a freezer. The resultant crystals are filtered and washed with ethyl acetate. The material is then purified by recrystallization from ethyl acetate and a 96.9% pure material is obtained. This material is maltyl tiglate.

Figure 7:
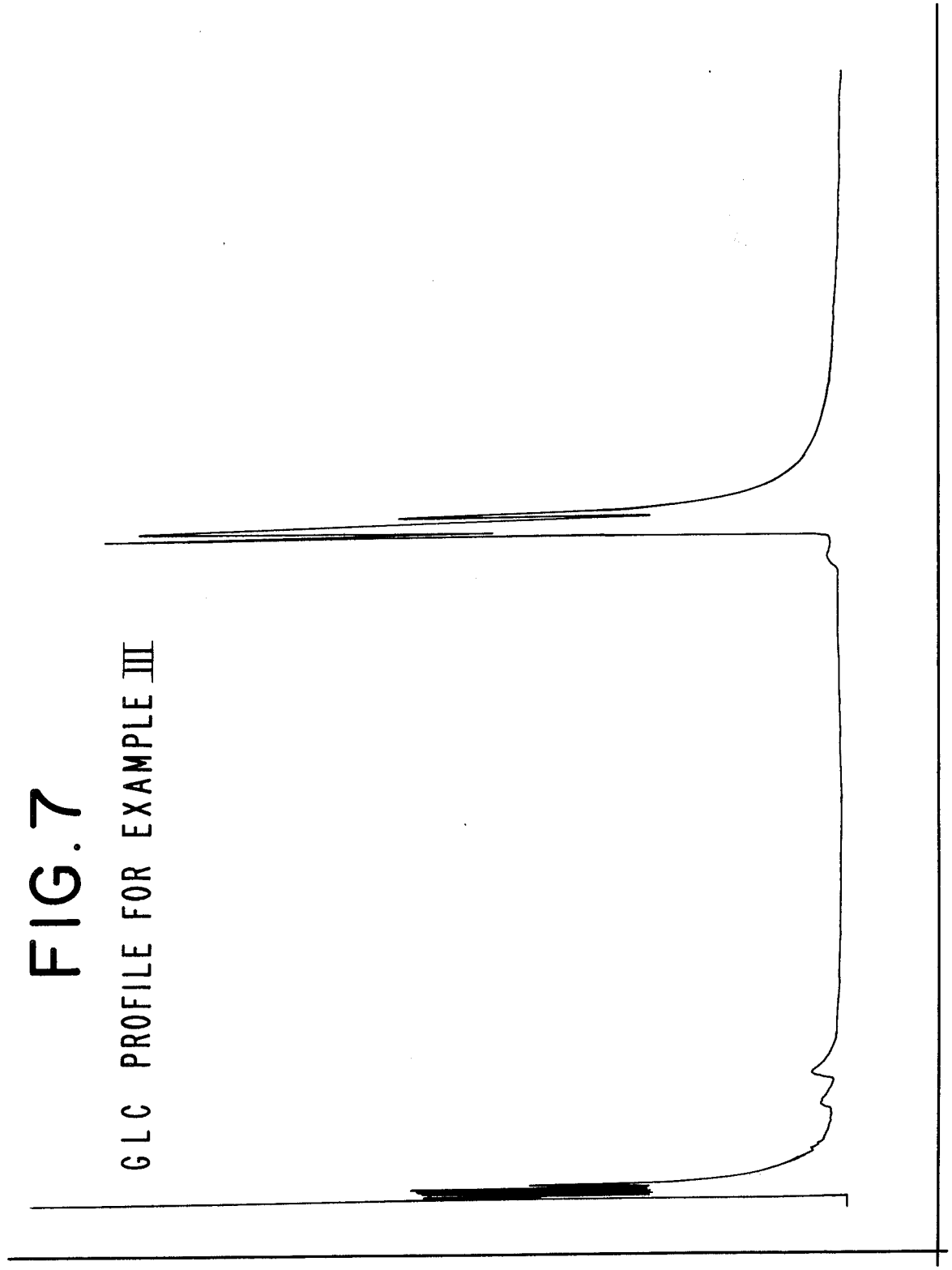
FIG. 7 represents the GLC profile for the reaction product of Example III, which is maltyl tiglate.

The GLC profile for the reaction product is set forth in FIG. 7. The NMR spectrum for maltyl tiglate is set forth in FIG. 8.

EXAMPLE IV

The following basic strawberry flavor formulation is prepared:

| Ingredients | Parts by Weight |
| --- | --- |
| Parahydroxy benzyl acetone | 2 |
| Vanillin | 15 |
| Maltol | 20 |
| Ethyl methyl phenyl glycidate | 15 |
| Benzyl acetate | 20 |
| Ethyl butyrate | 10 |
| Methyl cinnamate | 5 |
| Methyl anthranilate | 5 |
| Alpha ionone | 1 |
| Gamma undecalactone | 2 |
| Diacetyl | 2 |
| Anethole | 1 |
| Cis-3-hexenol | 17 |
| Ethyl alcohol (95% aqueous food grade) | 385 |
| Propylene glycol | 500 |

At the rate of 6%, to half of the above-mentioned formulation, maltyl-2-methyl-3-pentenoate prepared according to Example I (C.A.S. name: 3-hydroxy-2-methyl-4H-pyran-4-one) is added. The basic strawberry formulation with the maltyl-2-methyl-3-pentenoate is compared to the basic strawberry formulation without said maltyl-2-methyl-3-pentenoate. Both flavors are compared at the rate of 50 ppm in water and evaluated by a bench panel composed of five individuals. The flavor containing the maltyl-2-methyl-3-pentenoate is found to have a sweet, fresh, more strawberry-like aroma and taste. Therefore, it is preferred unanimously by the members of the bench panel as being more pleasant, more characteristic and as the better strawberry flavor.

EXAMPLE V

PREPARATION OF MALTYL-2-METHYL-CIS-3-PENTENOATE

Reaction:

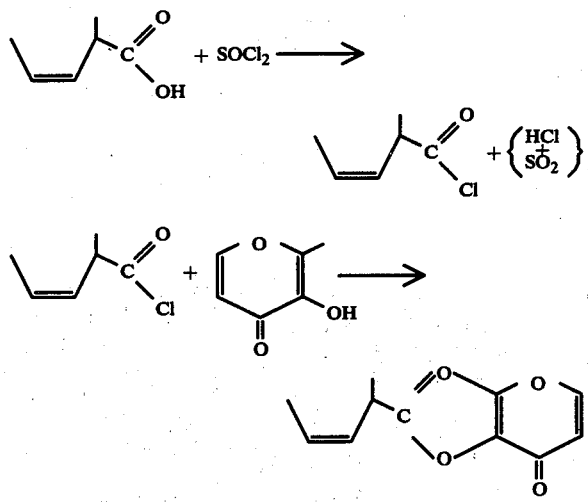

Thionyl chloride is immediately distilled before use (76° at 760 mm pressure) and added to 2-methyl-cis-3-pentenoic acid prepared according to Example XIV at column 30 of U.S. Pat. No. 3,984,579 issued on Oct. 5, 1976. A 1 liter three necked round bottomed flask equipped with a Fredrich's condenser, mechanical stirrer and heating mantle is then used for the reaction. The mixture of 2-methyl-cis-3-pentenoic acid and thionyl chloride is stirred and heated for a period of 1.5 hours (until no more sulfur dioxide or hydrogen chloride gas is emitted). A trap is then connected to the side arm of the Fredrich's condenser and vented into a beaker containing a 5% solution of sodium bicarbonate to trap the evolved hydrogen chloride and sulfur dioxide. The mixture is then allowed to cool to room temperature and 126 grams of maltol in 200 cc of benzene is added. The reaction mass is then heated to reflux for a period of one hour and then cooled. The unreacted 2-methyl-cis-3-pentenoic acid is extracted with 10 equal volumes of 5% sodium carbonate. The resulting reaction product is then washed with water. The resulting mixture is then filtered and the solid is determined to be unreacted maltol (27.44 grams or 44.76%). The benzene is then removed from the supernatant liquid by means of a rotary evaporator, gas chromatography indicating that there remains some 2-methyl-cis-3-pentenoic acid and benzene. The resulting product was purified by means of vacuum distillation whereby the benzene and 2-methyl-cis-3-pentenoic acid are removed. The impurities are distilled off at 4 mm Hg pressure at 70°–80° C. The maltyl-2-cis-3-pentenoate resulting is greater than 99% pure. Yield=114.01 grams or 51.36%.

The sodium carbonate layer is acidified with 2 molar hydrochloric acid and extracted with three 10% volumes of diethyl ether and concentrated to yield 18.9 grams of 34.08% residual 2-methyl-3-pentenoic acid.

GLC, NMR, IR and Mass Spectral data indicate that the material is maltyl-2-methyl-cis-3-pentenoate.

EXAMPLE VI

The following concentrate is prepared:

| Ingredients | Parts by Weight |
|---|---|
| Geraniol | 1.0 |
| Ethyl methyl phenyl glycidate | 3.0 |
| Maltyl-2-methyl-2-pentenoate prepared according to Example II | 5.0 |
| Vanillin | 6.0 |
| Ethyl pelargonate | 13.0 |
| Isoamyl acetate | 14.0 |
| Ethyl butyrate | 58.0 |

The resulting concentrate is dissolved in four volumes of propylene glycol and the mixture is added to a hard candy melt at the rate of 1.5 ounces of the concentrate in 100 pounds of melt. After the finished candy has been produced, it is found to have an excellent strawberry flavor. When the candy is compared with candy made under the same conditions but either (i) without the maltyl-2-methyl-2-pentenoate or (ii) with maltyl tiglate prepared according to Example III, it is found to have an inferior strawberry flavor.

EXAMPLE VII

The following concentrate is prepared:

| Ingredients | Parts by Weight |
|---|---|
| Geraniol | 1.0 |
| Ethyl methyl phenyl glycidate | 3.0 |
| Maltyl-2-methyl-cis-3-pentenoate prepared according to the process of Example V | 5.0 |
| Vanillin | 6.0 |
| Ethyl pelargonate | 13.0 |
| Isoamyl acetate | 14.0 |
| Ethyl butyrate | 58.0 |

The resulting concentrate is dissolved in four volumes of propylene glycol and the mixture is added to a hard candy melt at the rate of 1.5 ounces of the concentrate in 100 pounds of melt. After the finished candy has been produced, it is found to have an excellent strawberry flavor. When the candy is compared with candy made under the same conditions but either (i) without the maltyl-2-methyl-cis-3-pentenoate or (ii) with maltyl tiglate prepared according to Example III, it is found to have an inferior strawberry flavor.

EXAMPLE VIII

PART A: PREPARATION OF FLAVOR CAPSULES

Five hundred grams of water are heated to boil and 500 grams of dextrin (National Starch and Chemical Corporation, 78-1523) is added with rapid and efficient mixing, using a closed turbine, high shear mixer (Barrington CONVERTI JET Model CJ-5B). Mixing is continued until a homogeneous solution is obtained.

PART B: PREPARATION OF FLAVOR CAPSULE COMPOSITION

81 Grams of maltyl-2-methyl-cis-3-pentenoate prepared according to Example I is emulsified in 300 grams of the shell composition solution (A) by means of a homogenizing mixer (Barrington CONVERTI JET Model CJ-5B operated as a closed turbine unit). At the start of the operation the temperature of the matrix composition solution is 20° C. and of the maltyl-2-methyl-cis-3-pentenoate 15° C. The mixing vessel is cooled during the operation of the mixer in order to prevent a rise in the temperature and to keep the temperature below 25° C.

PART C: CAPSULE FORMATION AND DEHYDRATION

One thousand grams of polyethylene glycol having an average molecular weight of 400 (Union Carbide Corporation, Carbowax 400) and at a temperature of about 25° C. is placed in a vessel equipped with a homogenizing mixer (Barrington CONVERTI JET Model CJ-5B operated as an open turbine unit). One hundred grams of the maltyl-2-methyl-cis-3-pentenoate produced according to Example I is introduced into the polyethylene glycol in a thin stream with steady medium speed operation of the mixer (about 1,500 rpm shaft speed). By the action of the mixer, the maltyl-2-methyl-cis-3-pentenoate is broken up into coarse liquid particles, which in contact with the polyethylene glycol, are rapidly converted into gel particles and finally into virtually anhydrous capsule granules.

The capsule granules are separated from the excess polyethylene glycol by means of a basket centrifuge and added to chewing gum, toothpaste, chewable vitamin tablets and chewing tobacco as set forth infra.

EXAMPLE IX

The following mixture is prepared:

| Ingredient | Parts by Weight |
|---|---|
| Liquid Flavor Composition of Example IV | 48.4 |
| Cab-O-Sil M-5 (Brand of Silica produced by the Cabot Corporation of 125 High Street, Boston, Mass. 02110; Physical Properties: Surface Area: 200m$^2$/gm Nominal Particle Size: 0.012 microns Density: 2.3 lbs./cu.ft.) | 3.2 |

The Cab-O-Sil is dispersed in the liquid flavor composition of Example IV with vigorous stirring, thereby resulting in a viscous liquid. 48.4 Parts by weight of the encapsulated flavor composition of Example VIII is then blended into said viscous liquid, with stirring at 25° C. for a period of 30 minutes, resulting in a thixotropic sustained release flavor paste.

EXAMPLE X

CHEWING GUM

100 Parts by weight of chicle are mixed with 4 parts by weight of the flavor prepared in accordance with Example IX. 300 Parts by weight of sucrose and 100 parts by weight of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting strawberry flavor.

EXAMPLE XI

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example IX |
| 100.00 (Total) | |

PROCEDURE:

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant strawberry flavor, of constant strong intensity throughout said procedure (1-1.5 minutes).

EXAMPLE XII

CHEWABLE VITAMIN TABLETS

The flavor material produced according to the process of Example IX is added to a Chewable Vitamin Tablet Formulation at a rate of 9 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin B$_1$ (thiamine mononitrate) as Rocoat thiamine mononitrate 33 ⅓% (Hoffman La Roche) | 4.0 |
| Vitamin B$_2$ (riboflavin) as Rocoat riboflavin 33 ⅓% | 5.0 |
| Vitamin B$_6$ (pyridoxine hydrochloride) as Rocoat pyridoxine hydrochloride 33 ⅓% | 4.0 |
| Niacinamide as Rocoat niacinamide 33 ⅓% | 33.0 |
| Calcium pantothenate | 11.5 |
| Vitamin B$_{12}$ (cyanocobalamin) as Merk 0.1% in gelatin | 3.5 |
| Vitamin E (dl-alpha tocopheryl acetate) as dry Vitamin E acetate 33 ⅓% Roche | 6.6 |
| d-Biotin | 0.044 |
| Certified lake color | 5.0 |
| Flavor of Example IX | 5.0 |
| Sweetener - sodium saccharin | 1.0 |
| Magnesium stearate lubricant | 10.0 |

-continued

| | Gms/1000 tablets |
|---|---|
| Mannitol q.s. to make | 500.0 |

Preliminary tablets are prepared by slugging with flat-faced punches and grinding the slugs to 14 mesh. 13.5 Grams dry Vitamin A Acetate and 0.6 grams Vitamin D are then added as beadlets. The entire blend is then compressed using concave punches at 0.5 g each.

Chewing of the resultant tablets yields a pleasant, long-lasting, consistently strong strawberry flavor for a period of 12 minutes.

EXAMPLE XIII

CHEWING TOBACCO

Onto 100 pounds of tobacco for chewing (85 percent Wisconsin leaf and 15 percent Pennsylvania leaf) the following casing is spread at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example IX | 0.4 |

The resultant product is redried to a moisture content of 20 percent. On chewing, this tobacco has an excellent substantially consistent, long-lasting strawberry (20 minutes) nuance in conjunction with the main fruity tobacco note.

What is claimed is:

1. A maltyl-2-methyl-pentenoate having the structure:

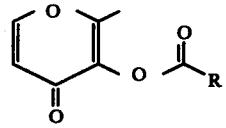

wherein R is a moiety selected from the group consisting of:

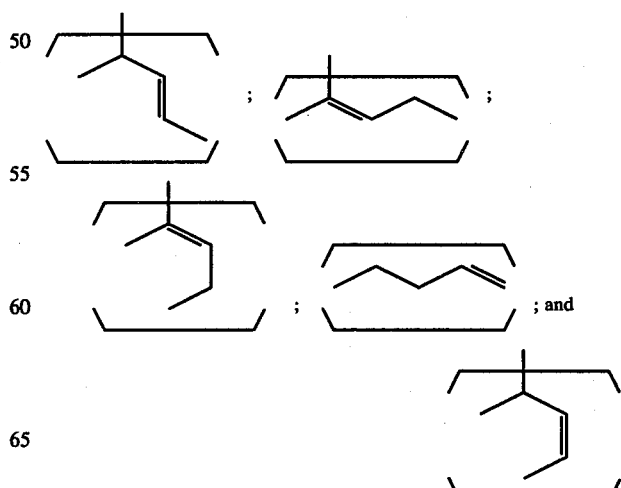

2. The maltyl-2-methyl-pentenoate of claim 1 wherein R has the structure:
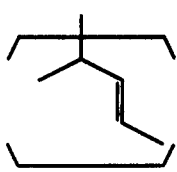
3. The maltyl-2-methyl-pentenoate of claim 1 wherein R has the structure:
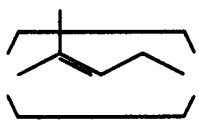
4. The maltyl-2-methyl-pentenoate of claim 1 wherein R has the structure:
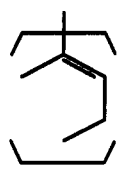
5. The maltyl-2-methyl-pentenoate of claim 1 wherein R has the structure:
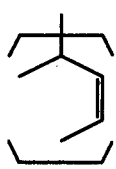
* * * * *